US009506099B2

(12) United States Patent
Palzer et al.

(10) Patent No.: US 9,506,099 B2
(45) Date of Patent: Nov. 29, 2016

(54) NATURAL TASTE ENHANCING SAVOURY BASE AND A PROCESS FOR ITS PREPARATION

(75) Inventors: Stefan Palzer, Lausanne (CH); David Nikolic, Bergheim (DE); Pieter Berends, Bodman-ludwigshafen (DE); Thang Ho Dac, Le Mont-s/lausanne (CH); Yvette Fleury Rey, Ursy (CH); Helge Ulmer, Bad Windsheim (DE)

(73) Assignee: Nestec S.A., Vevey (CH)

( * ) Notice: Subject to any disclaimer, the term of this patent is extended or adjusted under 35 U.S.C. 154(b) by 241 days.

(21) Appl. No.: 12/680,092

(22) PCT Filed: Jul. 17, 2008

(86) PCT No.: PCT/EP2008/059378

§ 371 (c)(1), (2), (4) Date: Mar. 25, 2010

(87) PCT Pub. No.: WO2009/040150

PCT Pub. Date: Apr. 2, 2009

(65) Prior Publication Data

US 2010/0196536 A1 Aug. 5, 2010

(30) Foreign Application Priority Data

Sep. 26, 2007 (EP) ..................................... 07117260

(51) Int. Cl.
| | |
|---|---|
| *A23L 1/23* | (2006.01) |
| *A23L 1/226* | (2006.01) |
| *C12P 19/32* | (2006.01) |
| *C12P 13/14* | (2006.01) |

(52) U.S. Cl.
CPC ............ *C12P 19/32* (2013.01); *A23L 27/2028* (2016.08); *A23L 27/21* (2016.08); *A23L 27/24* (2016.08); *C12P 13/14* (2013.01)

(58) Field of Classification Search
CPC .... A23L 27/2028; A23L 27/21; A23L 27/24
USPC .............................................. 426/52, 534, 7
See application file for complete search history.

(56) References Cited

U.S. PATENT DOCUMENTS

| | | | | |
|---|---|---|---|---|
| 3,268,415 | A * | 8/1966 | Misawa et al. ................. | 435/92 |
| 6,036,980 | A | 3/2000 | Beck et al. | |
| 6,838,100 | B2 | 1/2005 | Jaeger et al. | |
| 2003/0152684 | A1 | 8/2003 | Saito et al. | |
| 2004/0047955 | A1 * | 3/2004 | Arrendale et al. ............. | 426/262 |

FOREIGN PATENT DOCUMENTS

| | | | |
|---|---|---|---|
| EP | 0031162 | 7/1981 | |
| EP | 0181421 | 5/1986 | |
| EP | 0844308 | 5/1998 | |
| EP | 1016708 | 7/2000 | |
| EP | WO2006024464 A1 | 3/2006 | |
| EP | 2042043 | 4/2009 | |
| GB | 1107693 | 3/1968 | |
| JP | 10215891 | * 8/1998 | ............. C12P 13/14 |
| WO | WO2005013723 | 2/2005 | |
| WO | WO2005067734 | 7/2005 | |
| WO | 2006/024464 A1 | 3/2006 | |
| WO | 2007/101476 A1 | 9/2007 | |
| WO | WO2007101476 A | 9/2007 | |

OTHER PUBLICATIONS

JP-10-215-891—Machine Translation.*
Moio, L. et al. 1998. Grana Padona cheese aroma. J. Dairy Res. 65: 317-333.*
Demyttenaere, J. et al. 2002. The chemistry of the most important maillard flavor compounds of bread and cooked rice. American Chemical Society. pp. 1-16.*
Nara, T. et al. 1968. Biotechnol. Bioeng. 10: 277-289.*
Owens, J. D. et al. 1997. J. Sci. Food Agric. 74: 132-140.*
Anonymous: Production Process, "Amino acids are made from natural materials"—Encyclopedia of Amino Acids: Production of mono sodium glutamate by fermentation [Online] XP002469588 Retrieved from the Internet: URL:http://www.ajinomoto.com/amino/eng/product_print.html> [retrieved on Feb. 19, 2008].
International Search Report—PCT/EP2008/059378 mailed Aug. 27, 2008, 3 pages.
Written Opinion of the International Searching Authority PCT/EP2008/05978 mailed Aug. 27, 2008, 5 pages.
Ault, Mar. 2004, pp. 347-355—Journal of Chemical Education—vol. 81, No. 3, Mar. 2004.
Elhariry et al., 2004, pp. 15-39—Res. Develo. Microbiology 8(2004) ISBN 7736-211-9.
Kirk, 1991, pp. 534-544—Encl. of chemical Technology, Fourth Edition, vol. 2.
Kirk, 1991, pp. 571-579—Encl. of Chemical Technology—Fourth Edition—vol. 2 1-1.
International Search Report and Written Opinion issued Aug. 27, 2008 for PCT/EP2008/059378.

* cited by examiner

*Primary Examiner* — Hamid R Badr
(74) *Attorney, Agent, or Firm* — K&L Gates LLP

(57) ABSTRACT

The invention concerns a cultured savory base with increased umami power comprising: up to 80% of naturally derived compounds taken in the group consisting of glutamate, IMP and GMP, naturally food derived compounds such as organic acids, amino acids, peptides and aroma compounds.

22 Claims, No Drawings

NATURAL TASTE ENHANCING SAVOURY BASE AND A PROCESS FOR ITS PREPARATION

The present invention concerns a natural shelf-stable taste enhancing savoury base and a process for its preparation.

The U.S. Pat. No. 6,838,100 concerns a process for the preparation of a cultured savoury base, which comprises hydrolyzing for a sufficient time to prepare a savoury material, a protein containing material using a combination of at least one enzyme with at least one thermotolerant lactic acid bacteria strain selected for its ability to provide a glutaminase activity (such that the base maintains glutaminase activity) in order to provide glutamic acid or a glutamate in the base in an amount sufficient to enhance body and taste. The umami taste obtained by following this way of procedure is not high enough. Therefore, it is necessary to add to these preparations purified MSG (Mono-Sodium-Glutamate) and nucleotides (IMP: Inosine Monophosphate and GMP: guanosine Monophosphate), or yeast extracts. The problem with such a procedure is that it is not natural or in the presence of yeast extract gives a yeasty taste to the final product.

It is therefore an object of the present invention to provide a natural food composition that is useful to provide easily and conveniently an improved umami taste to food preparations without the use of additives and the inconvenience of chemical aftertaste. The basic idea sustaining the present invention is to provide a taste enhancing savoury base that can be in any shelf stable and/or concentrated form and that may be used for seasoning meals and any type of savoury meals.

The present invention concerns a taste enhancing savoury base comprising:
  up to 80% of naturally derived compounds taken in the group consisting of glutamate, IMP and GMP,
  naturally food derived compounds such as organic acids, amino acids, peptides and aroma compounds.

According to the invention, all the above mentioned components (glutamate, IMP, GMP, the naturally food derived compounds) are of natural origin, present because of the raw products used in the process. In the present specification, we understand under naturally derived glutamate, IMP and GMP, that these compounds are obtained via at least one of the following way:
  extraction from raw material such as plant, animal or microorganism material,
  fermentation or
  biocatalysis.

Under glutamate, we understand glutamate anions in combination with any type of cations and/or free glutamic acid. Preferably, these cations are sodium or potassium cations. Under aroma compounds, we understand volatile compounds, like for example trimethylpyrazine, acetic acid or propionic acid.

All the percentages given below are in weight, based on the dry matter.

It is possible according to the invention to produce a savoury base with only glutamate, or IMP and/or GMP or any combination. In the first case, the amount of glutamate is comprised between 0.01 and 80% and in the second case, the content of IMP and GMP is comprised between 0.01 and 30%. When glutamate, IMP and/or GMP are present, the total amount varies between 0.01 and 80%.

The taste enhancing cultured savoury base comprises further
  sugars and
  macromolecules.

Under macromolecules, we understand polysaccharides, proteins and fats.

The type of sugars used according to the present invention is not critical. These sugars are of any type known in the art.

According to an embodiment of the invention, the quantity of natural glutamate, IMP and GMP is comprised between 10 and 80%. Preferably, this quantity is comprised between 10 and 60%, more preferably between 10 and 30%.

An important feature of the invention is that MSG, IMP and GMP are of natural origin. For determining the natural origin of these different components of the composition different techniques are possible. The most commonly used procedure is based on the isotopic 13C/12C ratio. For instance monosodium glutamate isolated from the product can be analysed using a Roboprep analyser coupled to a Europa 20-20 isotope ratio mass spectrometer which will chemically decompose monosodium glutamate (MSG) and the CO2 13C/12C isotope ratio is determined. In the case of a non natural MSG the 13C/12C isotope ratio will be lower than that for the natural one. The details concerning this type of measure is known from the man skilled in the art: see for example some details in Food Chemistry, Belitz-Grosch, Second Edition, pages 797-799, Abundance Ratios of Isotopes.

The savoury base provides improved umami sensory characteristics delivered in a natural way.

All the percentages in the present specification are given in weight.

The organic acids are mainly lactic acid, citric acid, acetic acid and malic acid.

The amino acids are mainly alanine, aspartic acid, glutamine, glutamic acid, glycine, leucine, lysine, methionine, tryptophan or valine.

The peptides are dipeptides, tripeptides or polypeptides.

Furthermore, the glutamate is not an added MSG, but natural glutamate, present on the base of the way of obtaining the cooking aid. The amount of glutamate is comprised between 10 and 80%. The amount of IMP and/or GMP is comprised between 0.01 and 15%.

NaCl is also present in the cooking aid according to the invention. The salt can be present naturally or can be also added, depending on the type of process and on the version concerned. The amount of salt can vary broadly.

The cooking aid further comprises between 0 and 20% of polysaccharides. These polysaccharides are taken from the group comprising derived cellulose, pectin, locust bean gum, starch, alone or in combination.

The shelf-stable cooking aid comprises further 0 to 70% of proteins. These protein are taken in the group comprising collagen, gelatine, myosin, actin, milk proteins, plant proteins, meat or fish proteins, alone or in combination. Further types of proteins are also possible.

Finally, the taste enhancing savoury base contains further at least one carbohydrate selected from the group comprising glucose, fructose, rhamnose, mannose, sorbitol, glycerol, maltodextrines alone or in combination. Further carbohydrates are also possible.

Another feature of the invention is the low amount of fat, which is comprised between 0 and 15%. More particularly, the cooking aid has a free fatty acid content comprised between 0 and 3.2%.

Different forms of presentation can be considered for the product according to the invention. It is possible to have the composition in any physical form, like cube, powder, paste, concentrate, granule or liquid.

The present invention concerns further the use of a taste enhancing savoury base as described above, wherein the base is comprised in food products taken from the group consisting of
- culinary products, such as bouillons, sauces, dehydrated soups,
- dry foods including snacks, cereals and biscuits,
- chilled and frozen products, like prepared meals,
- nutritional products,
- products for foodservice,
- flavours and flavour ingredients
- oral supplements,
- pet foods,
- beverages and
- any other products where glutamate is part of the composition.

The amount of this savoury base is comprised between 0.01 and 50% based on the total weight of said product.

The typical umami organoleptic descriptors for deliciousness according to trained panel have been identified and listed as follows:
- Fast Diffusion: corresponds to the first feeling that the consumer feels all over the mouth,
- Full Body: corresponds to well-balanced, appropriate levels of all flavour notes that result in a favourable, complete, mouth feeling sensation,
- Smoothness: corresponds to a smooth coating on the tongue,
- Salivation: this corresponds to the intensity of salivation that the product generates just after consumption,
- Retention: this is the post-consumption feeling that the product leaves in the mouth.

These five descriptors have been identified and are used to characterize and to hierarchise the different products made with the different ingredients used in different concentration.

It is noticeable that many descriptors refer to organoleptic features that are in relation not only with taste but are related to a textural effect. For example retention refers to a possible long interaction of the components of the stocks with the mouth mucus and epithelium on the tongue, where taste buds are located. So, one can notice that the deliciousness in the sense it is understood in the context of the present invention refers to a sensitive feeling that goes beyond the taste itself. The deliciousness may then be qualified as an interaction of taste with an occupation of the interior of the mouth thanks to an important or at least non-negligible textural effect.

There are different ways to use the cooking aid according to the invention. In the case of cubes, a paste or a powder, it is possible to add the cooking aid on the meal or in the meal, in a quantity depending on the taste wanted by the consumer. Normally, the cooking aid is added or mixed with the meal in a quantity of from 0.01 to 10% based on the total weight of the meal.

According to another feature, the invention concerns a method for bringing and/or enhancing taste in a meal by addition of a natural savoury base according to the invention in said meal in a quantity of from 0.01 to 50% based on the total weight of the meal.

According to a further feature, the invention concerns a process for the preparation of a taste enhancing savoury base as described before, comprising one or more of the processing steps described below:
- Fermentation on substrate using a microorganism of genus *Corynebacterium*, *Brevibacterium*, *Bacillus*,
- cell disruption which yields a crude extract including cell debris.

According to an embodiment of the process of the invention, removal of cells or cell debris by filtration and/or centrifugation can be carried out, which yields a cell free broth. It is also possible to mix the broth with a natural hydrolysate in a ratio ranging from 0 to 99%.

The fermentation is carried out for obtaining the required amount of glutamate, which is then mixed with the product obtained according to the process object of the U.S. Pat. No. 6,838,100 as mentioned in the beginning of the specification: that means a product obtained by hydrolysing a protein-containing material using a combination of at least one enzyme with at least one thermotolerant lactic acid bacteria strain selected for its ability to provide a glutaminase activity. In this process, the enzyme is an exo- or endo-protease, deaminase, carbohydrase or amyloglucosidase.

According to this way of proceeding, the fermentation is carried out in 20 hours to 72 hours, at a pH comprised between 5 and 9 and at a temperature comprised between 25 and 40° C.

According to another feature of the invention, the process is more directed to increase the IMP and GMP content. In this case, the process is the same as above, but with other parameters concerning the reaction procedure.

As before, the natural hydrolysate is the product obtained according to U.S. Pat. No. 6,838,100.

In the case to increase the IMP and GMP content, the fermentation is carried out in 3 to 6 days, at a pH comprised between 5 and 9 and at a temperature comprised between 25 and 40° C.

It is clear that by proceeding according to the process to obtain more glutamate, there is also a presence of nucleotides and vice versa for the process increasing the nucleotides content.

In both of the above mentioned processes, it is also possible prior to mix with the natural hydrolysate to spray or vacuum/belt-dry the broth and convert it into any physical form, like powder, paste, cubes.

The substrate is preferably a natural substrate. This natural substrate used is from a carbon or nitrogen source of any kind, provided that they are utilizable for the strain employed. As for the carbon source, monosaccharides or oligosaccharides, like glucose, fructose, mannose, sucrose, maltose, enzymatic hydrolysate of starch, molasses may be used separately or in combination of two or more. As for the nitrogen source, ammonia, urea, ammonium salts, like ammonium sulphate, amino acids, peptides, proteins, yeast extract, corn steep liquor, enzymatic hydrolysate of plant material or starch, meat or fish products may be used separately or in combination of two or more. Nutrients can be also added: these nutrients are for example phosphates, minerals or vitamins.

The plant material is taken from the group comprising wheat, corn, tapioca and rye.

The enzymatically treated starch is the starch of one of the above mentioned plants.

The following examples illustrate the invention in more details.

EXAMPLE 1

Enzymatically derived glucose is mixed with further substrates necessary for the growth of a microorganism.

This mixture is inoculated with a fairly high cell concentration of a microorganism belonging to the genus of *Corynebacterium*.

The fermentation is run between 20 and 48 hours, at a pH comprised between 5 and 9 and at a temperature between 25 and 40° C. During the fermentation with these parameters acids are excreted as a natural byproduct of the fermentation process.

The cells are inactivated via heat treatment and then separated by physical means from the fermentation medium, the naturally derived acids stay in the broth.

The fermentation broth can be mixed with a natural hydrolysate before being exposed to an evaporation step. In the following this concentrated paste is spray-dried.

EXAMPLE 2

A substrate is prepared as in example 1 and the fermentation is initiated with an inoculation according to example 1.

The fermentation is run between 3 and 6 days, at a pH comprised between 5 and 9 and at a temperature between 25 and 40° C. During the fermentation with these parameters nucleotides such as IMP and/or GMP are excreted as a natural byproduct of the fermentation process.

The fermentation broth is further processed in the same manner as in example 1.

EXAMPLE 3

The products with naturally derived components obtained in example 1 and 2 are mixed together before and/or after the drying process. The products from example 1 and example 2 are mixed with a natural hydrolysate in order to obtain the best ratio for intense umami taste without off flavour for certain applications, e.g. in soups. The natural hydrolysate serves as base and is added in an amount of up to 50%. This hydrolysate is mixed with 25% of product from example 1 and 25% of product from example 2. The mixed product is applied in culinary products in an amount depending on the type of application. For example, in the case of soup, the above mentioned product is added in an amount of around 2% and in the case of sauces, it is added in the amount of around 20%. The umami taste resulting from the application of the above described product is more intense than applying any commercially available and artificial taste enhancers.

EXAMPLE 4

The products according to example 1 and example 2 are mixed together before and/or after the drying process. The mixed powder is applied for a GC-MS analysis to determine the flavour active compounds. Therefore a Solid-Phase-microextraction (SPME) was used, and a sample of the headspace is injected.

The following compounds are present: Trimethylpyrazine, Acetic acid, Propionic acid.

EXAMPLE 5

A sensory evaluation in culinary product application of a mixture of the powders described in Examples 1 and 2 resulted in the following outcome: an umami intensity that can be compared 1:1 to the usage of the same weight amount of pure MSG.

The invention claimed is:
1. A process for the preparation of a taste enhancing savory base comprising between 0.01 and 80% of naturally derived compounds selected from the group consisting of glutamate, IMP and GMP, amino acids in which alanine, aspartic acid, glutamine, glutamic acid, glycine, leucine, lysine, methionine, tryptophan and valine are a majority of the amino acids, and naturally food derived compounds selected from the group consisting of trimethylpyrazine, propionic acid, and combinations thereof, the process comprising:
 producing a first product by fermenting a first substrate using a microorganism of *Corynebacterium* for 20 to 48 hours, at a pH between 5 and 9 and at a temperature between 25 and 40° C.;
 producing a second product by fermenting a second substrate using a microorganism of *Corynebacterium* for 3 to 6 days, at a pH between 5 and 9 and at a temperature between 25 and 40° C.; and
 mixing the first product with the second product.

2. The process according to claim 1, comprising removing cells or cell debris from at least one product selected from the group consisting of the first product and the second product by a step selected from the group consisting of filtration and centrifugation.

3. The process according to claim 1, comprising
 mixing a natural hydrolysate with at least one product selected from the group consisting of the first product and the second product.

4. The process according to claim 3, wherein the natural hydrolysate is 50% of the taste enhancing savory base by weight.

5. The process according to claim 4, wherein the first product is 25% of the taste enhancing savory base by weight, and the second product is 25% of the taste enhancing savory base by weight.

6. The process according to claim 3, wherein prior to mixing with the natural hydrolysate, at least one product selected from the group consisting of the first product and the second product is dried by a step selected from the group consisting of spray-drying and vacuum/belt-drying and converted into any physical form.

7. The process according to claim 1, wherein at least one substrate selected from the group consisting of the first substrate and the second substrate is selected from the group consisting of a carbon source and a nitrogen source.

8. The process according to claim 1, wherein at least one substrate selected from the group consisting of the first substrate and the second substrate is obtained by the enzymatic step selected from the group consisting of hydrolysis of a plant material and the enzymatic hydrolysis of starch.

9. The process according to claim 8, wherein the plant is selected from the group consisting of wheat, corn, tapioca, and rye, and the starch is the starch of one of the above mentioned plants.

10. A method for bringing and/or enhancing taste in a meal, the method comprising:
 fermenting a first substrate and a second substrate, each using a microorganism of *Corynebacterium* to obtain naturally derived compounds selected from the group consisting of glutamate, IMP and GMP, naturally food derived compounds selected from the group consisting of trimethylpyrazine and propionic acid, and amino acids in which alanine, aspartic acid, glutamine, glutamic acid, glycine, leucine, lysine, methionine, tryptophan and valine are a majority of the amino acids, the fermenting is performed for 20 to 48 hours at a pH between 5 and 9 and at a temperature between 25 and 40° C. for the first substrate, and for 3 to 6 days, at a pH between 5 and 9 and at a temperature between 25 and 40° C. for the second substrate;
 mixing the first fermented substrate with the second fermented substrate; and adding a natural savory base comprising the amino acids, the naturally food derived compounds, and between 0.01 and 80% of the naturally derived compounds to the meal in a quantity of from 0.01 to 50% based on the total weight of the meal.

11. A process for the production of a taste enhancing savory base comprising between 0.01 and 80% of naturally derived compounds selected from the group consisting of glutamate, IMP and GMP; amino acids in which alanine, aspartic acid, glutamine, glutamic acid, glycine, leucine, lysine, methionine, tryptophan and valine are a majority of the amino acids, and naturally food derived compounds selected from the group consisting of trimethylpyrazine, propionic acid, and combinations thereof, the process comprising:
producing a first product by fermenting a first substrate using a microorganism of *Corynebacterium* for 20 to 48 hours, at a pH between 5 and 9 and at a temperature between 25 and 40° C.;
producing a second product by fermenting a second substrate using a microorganism of *Corynebacterium* for 3 to 6 days, at a pH between 5 and 9 and at a temperature between 25 and 40° C.; and
mixing the first product with the second product.

12. The process according to claim 11, comprising removing cells or cell debris from at least one product selected from the group consisting of the first product and the second product by a step selected from the group consisting of filtration and centrifugation.

13. The process according to claim 11, comprising mixing the first product and the second product with a natural hydrolysate.

14. The process according to claim 13, wherein the natural hydrolysate is 50% of the taste enhancing savory base by weight.

15. The process according to claim 11, wherein the first product is 25% of the taste enhancing savory base by weight, and the second product is 25% of the taste enhancing savory base by weight.

16. The process according to claim 11, wherein prior to mixing with the natural hydrolysate at least one product selected from the group consisting of the first product and the second product is dried and converted into any physical form.

17. The process according to claim 11, wherein at least one substrate selected from the group consisting of the first substrate and the second substrate is selected from the group consisting of a carbon and nitrogen source.

18. The process according to claim 11, wherein at least one substrate selected from the group consisting of the first substrate and the second substrate is obtained by the enzymatic step selected from the group consisting of hydrolysis of a plant material and the enzymatic hydrolysis of starch.

19. The process according to claim 18, wherein the plant is selected from the group consisting of wheat, corn, tapioca, rye and the starch is the starch of one of the above mentioned plants.

20. The process according to claim 1, wherein the first product and the second product are present in the taste enhancing savory base at a ratio of 1:1 by weight.

21. The method according to claim 10, wherein the first fermented substrate and the second fermented substrate are present in the meal at a ratio of 1:1 by weight.

22. The process according to claim 11, wherein the first product and the second product are present in the taste enhancing savory base at a ratio of 1:1 by weight.

* * * * *